United States Patent [19]

Zetter

[11] 4,092,232
[45] May 30, 1978

[54] H₂S DIRECT GAS SENSOR

[75] Inventor: Mark S. Zetter, Santa Clara, Calif.

[73] Assignee: Dictaphone Corporation, Rye, N.Y.

[21] Appl. No.: 778,875

[22] Filed: Mar. 18, 1977

Related U.S. Application Data

[63] Continuation-in-part of Ser. No. 625,857, Oct. 28, 1975, abandoned.

[51] Int. Cl.² .............................................. G01N 27/46
[52] U.S. Cl. ................................ 204/195 P; 204/1 T
[58] Field of Search ........... 204/1 T, 1 P, 1 F, 195 R, 204/195 P

[56] References Cited

U.S. PATENT DOCUMENTS

| | | | |
|---|---|---|---|
| 2,278,248 | 3/1942 | Darrah | 204/195 R |
| 3,227,643 | 1/1966 | Okun et al. | 204/195 P |
| 3,493,484 | 2/1970 | Berg et al. | 204/195 R |
| 3,503,861 | 3/1970 | Volpe | 204/195 P |
| 3,785,948 | 1/1974 | Hitchman et al. | 204/195 P |
| 3,803,006 | 4/1974 | Krueger et al. | 204/195 P |
| 3,897,315 | 7/1975 | Riseman et al. | 204/1 T |

*Primary Examiner*—T. Tung
*Attorney, Agent, or Firm*—Limbach, Limbach & Sutton

[57] ABSTRACT

A combined specific ion and reference electrode structure having an air gap, gas permeable membrane and in which the active, conducting solution has a surface tension and boiling point which are great enough that with equal ambient pressures on both sides of the membrane the active solution will neither leak nor evaporate rapidly through the membrane at the temperature range over which the electrode structure is operated, namely −40° C to 60° C. In the preferred embodiment, the active solution solvent as well as the reference solution solvent are selected from among the class consisting of ethylene glycol, propylene glycol, dipropylene glycol, diethylene glycol, triethylene glycol, tetraethyleneglycol, hexylene glycol, propylene carbonate, dimethyl sulfoxide and dimethyl formamide.

17 Claims, 2 Drawing Figures

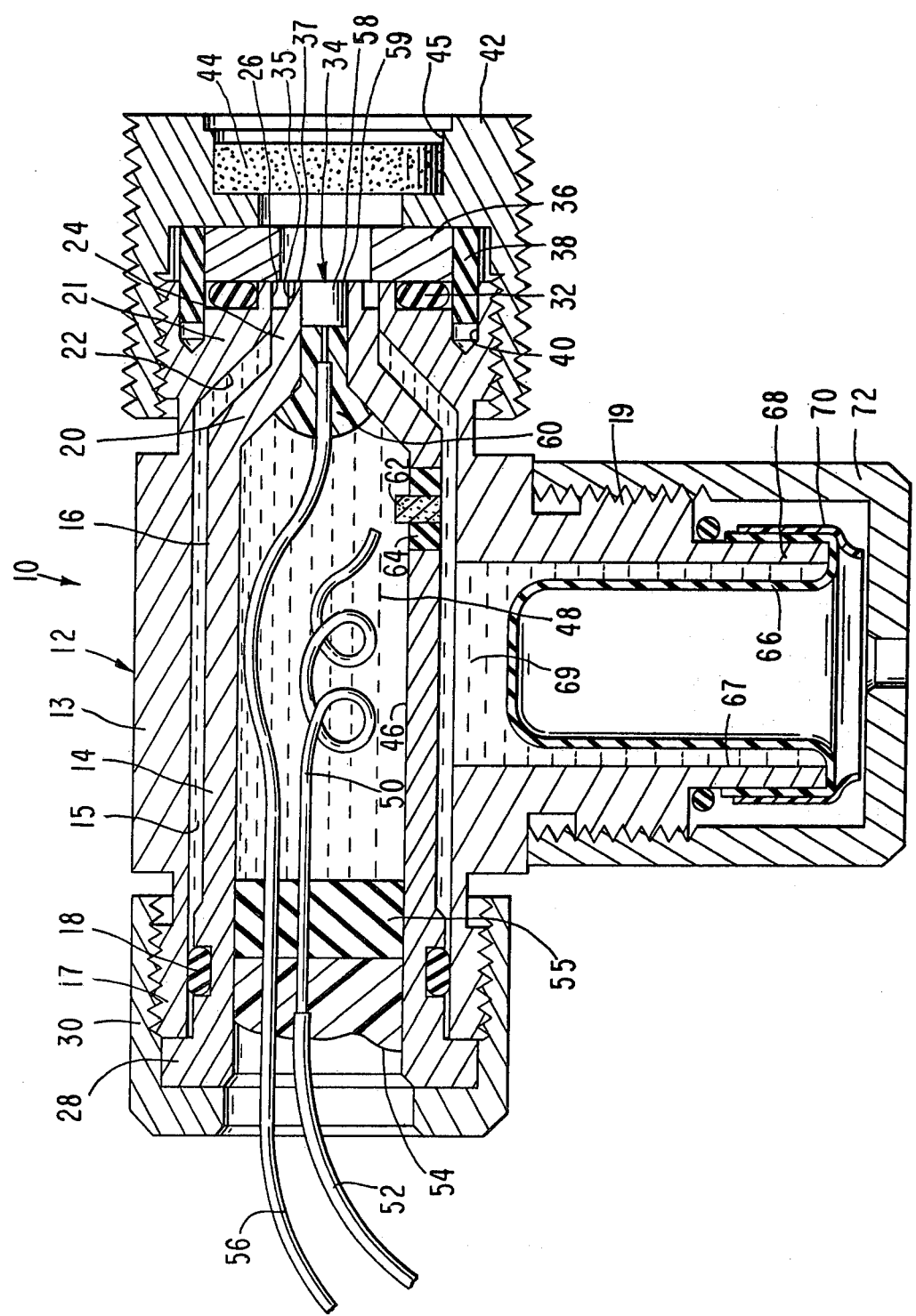
FIG._1.

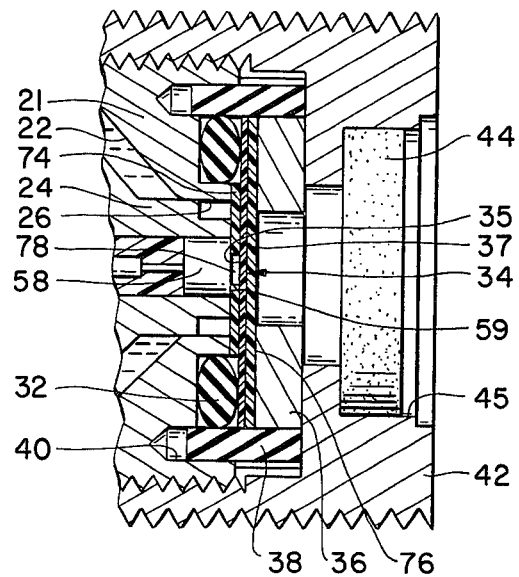
FIG._2.

H₂S DIRECT GAS SENSOR

CROSS-REFERENCE TO RELATED APPLICATION

This application is a continuation-in-part of my copending application, Ser. No. 625,857, filed Oct. 28, 1975 and entitled IMPROVED H₂S GAS SENSOR DEVICE, now abandoned.

BACKGROUND OF THE INVENTION

The present invention relates to a direct gas sensor and more particularly to a hydrogen sulfide direct gas sensor.

Hydrogen sulfide ($H_2S$) is an extremely toxic gas and exposure to concentrations of less than 0.1% in air for a few seconds can be fatal. The Occupational Safety and Health Act (OSHA) has stipulated that 10 parts per million (10 p.p.m.) is the maximum weighted-averaged limit that a person can be continuously exposed to in an 8-hour working day.

Hydrogen sulfide is found in many industrial environments, but is particularly prevalent in the petrochemical industry. It is necessary in such industries to have an accurate, low-cost, low maintenance $H_2S$ monitor which not only has a fast response time, on the order of less than 5 seconds, but also has a fast recovery time. Present day sensors are mostly solid state and are not particularly selective. For example, some such solid state sensors respond to ammonia. They typically have a slow response and if they have not been in contact with $H_2S$ for a day or two they can take up to four minutes to respond to the OSHA limit. Most $H_2S$ sensors require explosion proofing and must not be corrodible. Many types of prior art $H_2S$ sensors, besides being slow and cumbersome, also have to be checked out every day, particularly those sensors which use electrochemical methods. Furthermore, many such electrochemical type sensors are mechanically complex, requiring pumps, pressure monitors and the like.

One particular type of sensor electrode is known in the art as a specific ion probe. Typically, such specific ion probes utilize a specific ion electrode which is sensitive to the specific ion which is to be sensed, such as $S^=$. A specific ion electrode is utilized in conjunction with a reference electrode which may take a variety of forms. The reference electrode and the specific ion electrode are immersed in a solution in which the gas containing the specific ion is bubbled. The electrochemical reactions at the two electrodes produce a voltage in proportion to the logarithm of the concentration of the specific ion in the solution. The primary problem with such arrangements is that they generally require the probes to be immersed in the solution. These probes are also not particularly fast when the time required to introduce the gas into the solution is taken into account.

SUMMARY OF THE INVENTION

The above and other disadvantages of prior art gas sensing electrodes are overcome by the present invention of an improvement to a combined specific ion and reference electrode, gas sensing probe of the type having a single housing, the housing containing an reference solution, an electrolytic active solution, separate reservoirs for the reference solution and the active solution, porous means for restricted fluid communication between the separate reservoirs, a reference electrode disposed in the reference solution reservoir, a gas permeable, hydrophobic membrane mounted in an open end of the housing and having one surface exposed exterior of the housing and another surface exposed interior of the housing, a specific ion sensing element spaced closely adjacent to the interiorly exposed surface of the membrane, and means for providing fluid communication between the active solution reservoir, the interiorly exposed surface of the membrane, and the specific ion sensing element, such that a predetermined electrical potential exists between the reference electrode and the sensing element for a given concentration of a select gas in the ambient atmosphere at a constant ambient temperature. The improvement according to the invention comprises using a solvent in the active solution having a surface tension and boiling point which are great enough that with equal ambient pressures on both sides of the membrane the solvent will neither leak nor evaporate rapidly through the membrane at the temperature range over which such probes are operated. The active solution also includes a mixture of two or more buffers to compensate for humidity effects. The first buffer tends to increase the pH of the active solution with an increase in the ambient humidity and the second buffer has the opposite effect. The two buffers are mixed in a ratio such that the electrical potential between the reference electrode and the sensing element is substantially constant for a constant gas concentration and a constant temperature of the active and reference solutions despite a varying ambient humidity exterior of the membrane. In the preferred embodiment the first buffers are either a triethanolamine (TEA) or hydroxymethyl aminomethane. The second buffers are phosphates such as disodium hydrogen phosphate and potassium dihydrogen phosphate.

In the preferred embodiment, the ratio of the concentrations of TEA to the phosphate buffer is between 1.0 to 2.0.

The membrane is made of porous polytetrafluoroethylene known under the trade name of TEFLON. Fluids having a surface tension in excess of 30 dynes per centimeter will not leak through the membrane provided there is no pressure differential across the membrane. This produces what is known as an "air gap" membrane which is porous to the gases to be measured but which does not leak the electrode fluids. The particular membrane utilized has a thickness of about 127$\mu$m, a porosity of between 70 to 85% and a pore size of between 0.2$\mu$m and 1.0$\mu$m.

The solvent used in the active solution must also have a high dielectric constant, i.e., it must dissolve phosphate salts to give a conductive active solution. The electrolytic active solution, in addition to being conductive, should also have a relatively high boiling point, such as at least 150° C, and, when mixed with water, a relatively low freezing point, that is, down to approximately −40° C. The active solvent must also be stable at the pH used, that is, it must not degrade. In practice, the pH range of the liquid will vary from 7.5 to 8.5 when buffered. In the preferred embodiment, the active solution solvent as well as the reference solution solvent are selected from among the class consisting of ethylene glycol, propylene glycol, dispropylene glycol, diethylene glycol, triethylene glycol, tetraethylene glycol, hexylene glycol, propylene carbonate, dimethyl sulfoxide and dimethyl formamide.

For sensing $H_2S$, the reference electrode is silver/silver chloride, and the specific ion sensing element is silver sulfide. The reference solution contains potassium chloride saturated with silver chloride. The potassium chloride concentration can be from $10^{-5}$M to a saturated solution, although typically, a $10^{-2}$M to $10^{-3}$M solution is preferred. The reference solution solvent is preferably the same as the active solution solvent. The electrode housing is made of a synthetic material such as an acetal copolymer as, for example, the acetal copolymer known under the trade name of CELCON, a trademark of Celanese.

In the embodiments using liquids which are hydroscopic, such as ethylene glycol, it is necessary to provide a bladder arrangement made of silicon rubber or neoprene or any other elastomer which will expand as the active solution absorbs more water from the air.

Because of the high boiling point of the active solution solvents and their relatively high surface tension as compared to the porosity of the membrane, none of the active solution solvents will leak or evaporate rapidly through the membrane and thus the thin film of fluid between the active electrode and membrane will not dry out prior to the time that fluid communication is lost between the reference and active solution reservoirs due to an overall loss of the volume of the active solution. In prior art electrodes of this type, the evaporation rate of the active solvent is so great that the thin fluid film between the membrane and the sensing element dries out and becomes nonfunctional before there is any significant loss in the overall volume of the active solution solvent. In all of these embodiments, the gas being sensed, which in the preferred embodiment is $H_2S$, will pass through the semipermeable membrane and will dissolve in a thin layer of the active solution liquid which exists between the inner surface of the membrane and the sensing element. Once this happens, a known electrochemical reaction between the sensing element and the reference electrode takes place, involving the exchange of a specific ion of the gas to be detected, which in the peferred embodiment is $S^=$. This electrochemical reaction produces a voltage potential difference between the two electrodes which can be sensed to determine the extent of concentration of $H_2S$ exterior to the probe.

The chemical reaction taking place within the solution is as follows:

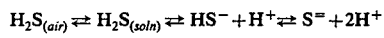

The chemical reaction taking place at the specific ion electrode is described as follows:

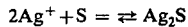

The extent of formation of $S^=$ in the solution depends on the pH of the solution thus the solution must be buffered. Too high a pH slows desorption and thereby raises the time required for the sensor to recover after being exposed to $H_2S$. Too low a pH lessens the extent of $S^=$ formation and thereby slows down the response time. The applicant has found that suitable buffering as described above will give the right pH balance of about 7.5 to 8.5, although other ranges will give a functioning system.

In order to fully appreciate the significance of this buffering feature, it is important to point out more clearly one of the problems which is overcome by the applicant's invention. The purpose of the selective ion probe structure of the applicant's design is to keep the signal of the sensor constant with varying humidity at constant ambient temperature (of the active and reference solutions) and constant gas concentration to which the probe is exposed. This means that the signal from the silver sulfide pellet of the active electrode must be constant without regard to pH changes since the reference electrode signal is constant at a constant temperature. It must be remembered that the pH of the active solution can change because of changes in humidity exterior to the selective ion probe. This is particularly true when a non-evaporative agent such as ethylene glycol is added to the active solution because ethylene glycol is hygroscopic. The factors that can effect the silver sulfide electrode signal with varying mixtures of ethylene glycol and $H_2O$, are the following:

(a) the solubility of the silver sulfide electrode in different ethylene glycol/$H_2O$ mixtures.

(b) the protonation constants of $H_2S$ in different ethylene glycol/$H_2O$ mixtures.

(c) the solubility of $H_2S$ in different ethylene glycol/$H_2O$ mixtures.

(d) the standard potential of the silver sulfide electrode in different ethylene glycol/$H_2O$ mixtures.

(e) the protonation constants of the buffers used in different ethylene glycol/$H_2O$ mixtures.

Factor (e), that is the protonation constants of the buffers used in the different ethylene glycol/$H_2O$ mixtures, can be selected empirically as the variable that is adjustable to offset the factors (a) – (d). By making the pH of the active solution change a predetermined amount in different ethylene glycol/$H_2O$ mixtures (i.e., different pH's) the effects of the factors (a) – (d) can be nulled so that the potential of the silver sulfide electrode, when immersed in the active solution, is constant with varying ambient humidity. Making the pH change by a predetermined amount is done by choosing a buffering system containing two or more buffers in an appropriate ratio.

In the preferred embodiment, this was done by empirically testing the pH changes of various buffers for changes in the ratio of ethylene glycol and water in the active solution. It was found that with triethanolamine the pH of the solution increased with an increase in the proportion of water in the active solution solvent, corresponding to an increase in the ambient humidity. With a phosphate buffer such as disodium hydrogen phosphate, for example, the pH of the active solution solvent decreased under the same conditions. By interpolating from the percentage changes in the magnitude of the pH of the active solution solvent for each buffer, a mixture of the two buffers was derived in a proportion which produced the desired result, i.e., a constant potential between the reference and sensor electrodes for a constant $H_2S$ concentrate despite an increase in the proportion of water in the active solution solvent. The exact proportion was more or less empirically determined.

The compensating effect of this buffer mixture can be illustrated by an example of how a change in one of the primary factors, factor "b" on page 8, is compensated by the buffer mixture. This can be better understood in the context of a discussion of a known type of selective ion probe, such as described in U.S. Pat. No. 3,897,315 (Riseman) which is used while submerged in a sample solution into which the gas to be sensed must be bubbled. The operation of such a probe is based on the assumption that the value of $[H^+]$ is a constant because of the pH buffer and the electrolyte. With $[H^+]$ constant the relationship $[S^=] = K_4[H_2S]$ is true, where $K_4$ is a function of the dissociation constants and $[H^+]^2$. For the Riseman type of cell operating in a solution into which the gas is dissolved, this may be true, however, in the applicant's device which is subject to the effects of humidity, this is not true. The constant referred to as $K_4$ in Riseman varies with varying concentrations of the ethylene glycol/$H_2O$ mixture in the applicant's probe. For example, if the dissociation constants decrease in value by a factor of 2 when the humidity goes from 10% to 90%, then it is necessary to choose a buffer mixture which will reduce $H^+$ by a factor of $1\sqrt{2}$ in order to keep $K_4$ constant. As mentioned above, this can be done by an appropriate choice of a buffer mixture, preferably having two or more buffers which have different (from each other) variations of their protonation constants for different concentrations of ethylene glycol/$H_2O$ mixtures. These buffers are then mixed together in a ratio which is selected to provide a combined protonation constant sufficient to compensate for the variation in $K_4$ with changes in humidity.

Once the humidity variation effect is nulled, the potassium chloride concentration in the reference cell is adjusted to make the isopotential of the cell correspond to the signal obtained at the most significant $H_2S$ value to be determined by use of the cell, which in the applicant's preferred embodiment is 10 parts/million.

The gas sensing probe according to the invention is extremely fast in its response and in its recovery time. It requires little or no maintenance as compared with prior art electrochemical probes. Furthermore, it does not require elaborate explosion proofing since it does not use any electromechanical devices, such as pump motors, which might produce a spark. Furthermore, there are no portions which will corrode.

It is therefore an object of the present invention to provide a probe for sensing gas in its gaseous state directly without the necessity for bubbling the gas through a solution.

It is another object of the invention to provide a direct gas sensing probe which has fast reaction and recovery rates.

It is a further object of the invention to provide an improved $H_2S$ direct gas sensing probe which is economical, lightweight and easily constructed.

It is still another object of the invention to provide an improved direct gas sensing $H_2S$ probe which is reliable and relatively maintenance free.

The foregoing and other objectives, features and advantages of the invention will be more readily understood upon consideration of the following detailed description of certain preferred embodiments of the invention, taken in conjunction with the accompanying drawing.

BRIEF DESCRIPTION OF THE DRAWING

FIG. 1 is a vertical view, partly in section and with portions broken away, of the preferred embodiment of the invention.

FIG. 2 is a vertical view, partly in section and with portions broken away, of a modification of the membrane structure of the preferred embodiment of the invention.

DETAILED DESCRIPTION OF CERTAIN PREFERRED EMBODIMENTS

Referring now more particularly to FIG. 1, there is shown a combined specific ion and reference electrode probe 10 having a hollow, T-shaped housing 12. The hollow cross arm 13 of the T-shaped housing 12 has a longitudinal bore 15 which partially contains a tubular, hollow insert 14. The main body portion of the insert 14 has an external diameter which is less than the interior diameter of the bore 15 so as to create an annular hollow space 16 between the exterior surface of the insert 14 and the interior surface of the bore 15. This hollow space 16 constitutes part of the reservoir for the active solution to be described in greater detail hereinafter.

The insert 14 is provided with an O-ring seal 18 near the outer end of the insert which seals off the annular space 16 from the exterior of the housing at one end 17, the left end as viewed in the drawing, of the T-shaped housing 12.

The insert 14 has a cone shape at its other end 20 which matches a cone shaped interior portion 22 of the bore 15 at an end 21 opposite from the end 17. The end of the cone shaped portion 20 includes a hollow, round, projecting neck 24 which loosely seats in a reduced diameter portion 26 of the bore 15 in the end 21 to provide fluid communication between the reservoir 16 and the opening of the bore 26 to the exterior. The insert 14 is provided with an annular flange 28 at the end opposite from the neck 26. The outer diameter of the flange 28 is greater than the inner diameter of the bore 15 and thus the annular flange 28 abuts against the opening to the bore 15. The insert 14 is held in place within the bore 15 by means of a cap 30 threaded onto the end 17 of the housing 12 over the flange 28.

The housing end 21 is provided with a recessed O-ring seal 32 surrounding the opening of the reduced diameter bore 26 to the exterior of the housing. A gas permeable membrane 34 which is hydrophobic, porous polytetrafluoroethylene, (such as a membrane known under the trade name of FLUOROPORE made by Millipore Corporation, Bedford, Massachusetts) is placed against the O-ring seal 32, convering the mouth of the bore 26. Thus, the membrane 34 has a surface 35 which faces towards the interior of the bore 26 and a surface 37 which faces towards the exterior of the housing 12. This membrane is about 127μm thick, has a porosity of between 70 and 85% and pore sizes of between 0.2μm and 1.0μm. A retaining ring 36, provided with a plurality of radially spaced, projecting pins 38, is fitted over the exterior surface 37 of the membrane 34. The pins 38 are received in bores 40 in the housing end 21 to prevent the ring 36 from rotating with respect to the membrane 34. A retainer cap 42 is threaded over the housing end 21 so as to press against the retaining ring 36 to hold it and the membrane in place. A porous polypropylene disc 44 is positioned in a bore 45 within the sensor cap 42 to allow gas to pass through to the membrane 34 while protecting the membrane from physical damage.

As mentioned above, the insert 14 is also hollow and contains a reservoir 46 for the reference electrolye 48. This electrolyte may be, for example, a 70-30 mixture of ethylene glycol and $H_2O$ with dissolved potassium chloride to $5 \times 10^{-3}M$ and saturated with silver chloride. A reference electrode 50 is also disposed within the reservoir 46. The reference electrode is preferably silver/silver chloride and is connected by means of an insulated wire 52 to the exterior of the housing 12 through the end cap 30.

A second insulated wire 56 passing through the end cap 30 also passes through the reservoir 46 and is connected to a specific ion sensor element 58 of silver sulfide fitted into the hollow neck 24 of the insert 14. The sensor element 58 has one end 59 flush with the end of the neck 24 to be closely adjacent to the membrane surface 35. The sensor element 58 is isolated from the reservoir 46 by an epoxy plug 60 formed around the insulated wire 56. The other end of the reservoir 46, near the housing end 17, is sealed with a rubber plug 55 and an epoxy plug 54 which both surround the wires 52 and 56.

A porous ceramic plug 62 is mounted in a rubber plug 64 in the wall of the body insert 14 so that restricted fluid communication is thereby provided between the reservoir 46 and the reservoir 16.

The portion 19 of the housing 12 which is perpendicular to the cross arm 13 also has a bore 67 which is in fluid communication with the reservoir 16. This bore 67 and the annular reservoir 16 are partially filled with the active solution 69. A rubber bladder 66 is fitted over the open end 68 of the bore 67 and is held in place at the open end by a heat shrunk tubing 70 fitted about the outside of the mouth of the opening at the end 68 and over the edge of the rubber bladder 66. The purpose of this bladder is to allow for expansion or contraction in the volume of the active solution 69 within the reservoir 16 and bore 67 due to absorption or desorption of moisture from the external environment. It should be pointed out that not all of the active solutions noted hereinafter are hydroscopic. A cap 72 is threaded over the open end 68 of the housing 12 to protect this bladder from disturbance.

Up to this point, the description of the combined electrode corresponds in some respects to known types of electrodes. However, such other electrodes are only capable of sensing gas when bubbled through an exterior solution, as described above at page 3. In contrast to this prior art requirement, the combined electrode of the present invention is capable of sensing gas directly in its gaseous state without the requirement that the gas be first dissolved in a liquid solution exterior of the sensing probe.

One of the primary factors which enables the present electrode to be usable in a direct gas sensing mode is the selection of the active solution solvent and reference solution solvent. These fluids are selected for their high boiling point, low freezing point, high dielectric constant and for a surface tension which prevents them from leaking through the gas permeable membrane 34. They must also not degrade when buffered to a pH of between 7.5 and 8.5. The liquids which have been found suitable for use as the active solution solvent, are the following:
ethylene glycol
propylene glycol
dipropylene glycol
diethylene glycol
triethylene glycol
tetraethylene glycol
hexylene glycol
propylene carbonate
dimethyl sulfoxide
dimethyl formamide.

All of these liquids, some when mixed with water, have a freezing point which is not greater than −40° C and a boiling point which is at least 150° C. They all have a surface tension range which is greater than 30 dynes per centimeter which, for the particular membrane utilized, will prevent the fluids from leaking through the membrane provided there are equal pressures on opposite sides of the membrane.

As stated above, potassium chloride to $10^{-2}$ to $10^{-3}$M is dissolved in the reference solvent and silver chloride is added until saturation is achieved. Various buffers are added to the active solvent to help eliminate humidity effects and the pH sensitivity. The particular buffers utilized in the preferred embodiment of the invention are triethanolamine (TEA) and phosphate buffers such as disodium hydrogen phosphate and potassium dihydrogen phosphate. In place of the TEA could be substituted Tris (hydroxymethyl) aminomethane. The preferred ratio of concentrations of TEA to phosphate buffers in the active solution is between 1.0 and 2.0. One example of buffer concentrations in the active solution using ethylene glycol as the solvent is 0.10 M phosphate and 0.15 M TEA. In this example, the reference and active solution solvents were ethylene glycol mixed with $H_2O$ in the ratio of 7:3, respectively.

It should be apparent that in the above described combined electrode, the physical configuration of the electrode is of secondary importance to the choice of fluids for the reference and active solution solvent and in other embodiments other physical configurations would also be suitable provided that the active sensor element 58 is positioned in contact with or immediately adjacent to the interior surface 35 of the membrane 34 so that a thin layer of active solution exists between the end 59 of the sensor element and the interior surface 35 of the membrane. The gas to be sensed will dissolve in this thin layer to set up the electrochemical reaction and the thinness of the fluid layer thus has a great effect on the reaction time of the probe. The thinner the layer, the faster the response time. Prior art selective ion probes are incapable of this function because they use liquids which either evaporate rapidly or leak through the membrane due to their low surface tension or low boiling points.

While certain concentrations and pH ranges have been specified herein, in other, less advantageous embodiments, other concentrations and ranges may be utilized.

While the invention has been described with respect to an $H_2S$ sensor, the teachings of the invention can be applied to other gas sensors of the electrochemical probe type by suitable changes in the sensing element and active solution. Furthermore, in some embodiments, other than for $H_2S$ sensing, the reference and active solutions can be combined into a single, conductive internal filling solution.

While a particular type of membrane has been specified, another type of suitable membrane 34 is hydrophobic, microporous polypropylene, such as that marketed under the trademarks "Celgard 2400∞, "Celgard 2402" and "Celgard 2500", all registered to the Celanese Plastics Company. The dimensions of Celgard 2400 are, for example, 25.4 μm thickness, pore sizes of 0.2 μm × 0.20 μm and a porosity of 38%.

Referring now to FIG. 2, a modification of the embodiment depicted in FIG. 1 is illustrated. In the modified version a C-shaped spacer 74 is located between the inner surface 35 of the membrane 34 and the end 59 of the sensor element 58. The circumferential opening 78 of the C-shaped spacer establishes a fluid path to the bore 26 to wet the surface 35 of the membrane 34 with the active solution 69.

The spacer 74 is made of a hydrophilic polypropylene, such as the type marketed under the trademark "Celgard 3501" by Celanese Plastics Company. The spacer 74 is 25μm (1 mil) thick. A protective membrane 76 is located between the outer surface 37 of the membrane 34 and the retaining ring 35. The protective membrane 76 has a high tensile strength in contrast to the membrane 34, which is "floppy". The membrane 76 is stretched taut or rigid during mounting. It is made of hydrophobic, microporous polypropylene, such as that marketed under the trademark "Celgard 2402" by Celanese Plastics Company. The thickness of the membrane 76 is 51μm (2 mils).

The purpose of this modification is to ensure that a thin layer of the active solution 69 of a predetermined thickness range, i.e., approximating the thickness of the spacer 74, exists between the end 59 of the sensor element 58 and the interior surface 35 of the membrane 34.

The terms and expressions which have been employed herein are used as terms of description and not of limitation, and there is no intention, in the use of such terms and expressions, of excluding equivalents of the features shown and described, or portions thereof, it being recognized that various modifications are possible within the scope of the invention claimed.

What is claimed is:

1. An improved electrochemical electrode structure of the potentiometric type having a single housing, the housing containing a reference electrolytic solution, an active electrolytic solution, separate reservoirs for the reference solution and the active solution, porous means for restricted fluid communication between the separate reservoirs, a reference electrode disposed in the reference solution reservoir, a gas permeable, hydrophobic membrane having one surface exposed to the exterior of the housing and another surface exposed to the interior of the housing, a sensing element spaced closely adjacent to the surface of the membrane exposed to the interior of the housing, and means for providing fluid communication between the active solution reservoir, the surface of the membrane exposed to the interior of the housing and the sensing element, such that a predetermined electrical potential exists between the reference electrode and the sensing element for a given concentration of a select gas in the ambient atmosphere at a constant ambient temperature, and wherein the improvement comprises a buffer mixture within the active solution to maintain the electrical potential between the reference electrode and the sensing element substantially constant for a constant temperature of the active and reference solutions despite a varying ambient humidity exterior of the membrane, and wherein the buffer mixture includes phosphates and a buffer selected from the group consisting of triethanolamine and hydroxymethyl aminomethane.

2. An improved electrochemical electrode structure as recited in claim 1, wherein the active solution includes a solvent which is selected from the group consisting of aqueous ethylene glycol, propylene glycol, dipropylene glycol, diethylene glycol, triethylene glycol, tetraethylene glycol, hexylene glycol, propylene carbonate, dimethyl sulfoxide and dimethyl formamide.

3. An improved electrochemical electrode structure as recited in claim 1, wherein the reference solution includes a solvent which is selected from the group consisting of aqueous ethylene glycol, propylene glycol, dipropylene glycol, diethylene glycol, triethylene glycol, tetraethylene glycol and hexylene glycol.

4. An improved electrochemical electrode structure as recited in claim 3, wherein the reference solution contains a dissolved alkali metal chloride ion and is saturated with silver chloride.

5. An improved electrochemical electrode structure as recited in claim 1, wherein the phosphate of the buffer mixture includes disodium hydrogen phosphate.

6. An improved electrochemical electrode structure as recited in claim 1, wherein the phosphate of the buffer mixture includes potassium dihydrogen phosphate.

7. An improved electrochemical electrode structure as recited in claim 1, wherein the membrane is made of polytetrafluoroethylene and has a thickness of between 90 to 170μm, a porosity of between 70% to 85%, and a pore size of 0.2μm to 1.0μm.

8. A probe for directly sensing gas in its gaseous state, the probe being an electrochemical electrode structure of the potentiometric type comprising a housing, the housing containing an electrolytic reference solution, an electrolytic active solution, separate reservoirs for the reference solution and the active solution, means for restricted fluid communication between the separate reservoirs, a reference electrode disposed in the reference solution reservoir, a microporous gas permeable, hydrophobic membrane having one surface exposed to the interior of the housing, a sensing element spaced closely adjacent to the interiorly exposed surface of the membrane, and means for providing fluid communication between the active solution reservoir, the interiorly exposed surface of the membrane, and the sensing element, such that a predetermined electrical potential exists between the reference electrode and the sensing element for a given concentration of a select gas in the ambient atmosphere at a constant ambient temperature and humidity, and the active solution including a buffer mixture comprising a first buffer which tends to increase the pH of the active solution with an increase in the ambient humidity surrounding the electrode structure and a second buffer which tends to have the opposite effect, the first and second buffers being combined in a proportion which causes the electrical potential between the reference electrode and the sensing element to be substantially constant for a constant ambient gas concentration and a constant temperature of the active and reference solutions despite a varying ambient humidity exterior of the membrane.

9. An improved electrochemical electrode structure as recited in claim 8, wherein the second buffer includes disodium hydrogen phosphate.

10. An improved electrochemical electrode structure as recited in claim 8, wherein the second buffer includes potassium dihydrogen phosphate.

11. An improved electrochemical electrode structure as recited in claim 8, wherein the first buffer includes triethanolamine.

12. An improved electrochemical electrode structure as recited in claim 8, wherein the first buffer includes hydroxymethyl aminomethane.

13. An improved electrochemical electrode structure as recited in claim 8, wherein the active solution includes a solvent which is selected from the group consisting of aqueous ethylene glycol, propylene glycol, dipropylene glycol, diethylene glycol, triethylene glycol, tetraethylene glycol, hexylene glycol, propylene carbonate, dimethyl sulfoxide and dimethyl formamide.

14. An improved electrochemical electrode structure as recited in claim 8, wherein the reference solution includes a solvent which is selected from the group consisting of aqueous ethylene glycol, propylene glycol, dipropylene glycol, diethylene glycol, triethylene glycol, tetraethylene glycol and hexylene glycol.

15. An improved electrochemical electrode structure as recited in claim 8, wherein the reference solution includes a dissolved alkali metal chloride ion and is saturated with silver chloride.

16. An improved electrochemical electrode structure as recited in claim 8, wherein the improvement further comprises a hollow spacer of hydrophilic synthetic material interposed between the interiorly exposed surface of the microporous membrane and the sensing element to accommodate a film of the active solution which is approximately the thickness of the spacer.

17. A sensor for detecting airborne $H_2S$ gas, the sensor comprising an electrochemical electrode structure of the potentiometric type having a housing, the housing containing a reference solution which contains a dissolved alkali metal chloride ion and is saturated with silver chloride, a conductive active solution, separate reservoirs for the reference solution and the active solution, porous means for restricted fluid communication between the separate reservoirs, a silver/silver chloride reference electrode disposed in the reference solution, a gas permeable, hydrophobic membrane having one surface exposed to the exterior of the housing and another surface exposed to the interior of the housing, a silver sulfide sensing element spaced closely adjacent to the interiorly exposed surface of the membrane, and means for providing fluid communication between the active solution reservoir, the interiorly exposed surface of the membrane, and the sensing element, such that a predetermined electrical potential exists between the reference electrode and the sensing element for a given concentration of $H_2S$ gas in the ambient atmosphere at a constant ambient temperature, and wherein the active solution includes a buffer mixture whose $1/\sqrt{H^+}$ varies linearly with the dissociation constants of $H_2S$ in the active solution due to changes in the ambient humidity surrounding the electrode structure, whereby the electrical potential between the reference electrode and the sensing element is maintained substantially constant for a constant temperature of the active and reference solutions despite a varying ambient humidity exterior of the membrane.

* * * * *